(12) United States Patent
Fabian

(10) Patent No.: US 7,399,899 B2
(45) Date of Patent: Jul. 15, 2008

(54) ATTACHMENT OF ELECTRONIC TAGS TO SURGICAL SPONGES AND IMPLEMENTS

(76) Inventor: Carl E. Fabian, 577 NE. 96th St., Miami Shores, FL (US) 33138

( * ) Notice: Subject to any disclaimer, the term of this patent is extended or adjusted under 35 U.S.C. 154(b) by 913 days.

(21) Appl. No.: 10/650,377

(22) Filed: Aug. 28, 2003

(65) Prior Publication Data
US 2005/0049564 A1   Mar. 3, 2005

(51) Int. Cl.
*A61F 13/15* (2006.01)
*A61F 13/00* (2006.01)

(52) U.S. Cl. .......................... 604/362; 602/41

(58) Field of Classification Search ................. 604/362, 604/41–79; 602/41–79
See application file for complete search history.

(56) References Cited

U.S. PATENT DOCUMENTS

| | | | | |
|---|---|---|---|---|
| 3,698,393 A * | 10/1972 | Stone | ........................... | 604/362 |
| 4,193,405 A * | 3/1980 | Abels | ........................... | 604/362 |
| 4,205,680 A * | 6/1980 | Marshall | ...................... | 604/362 |
| 4,658,818 A * | 4/1987 | Miller et al. | .................... | 606/1 |
| 5,041,103 A * | 8/1991 | Rupinskas | .................. | 604/362 |
| 5,057,095 A | 10/1991 | Fabian | ......................... | 604/362 |
| 5,105,829 A | 4/1992 | Fabian et al. | ................. | 128/899 |
| 5,107,862 A | 4/1992 | Fabian et al. | ................. | 128/899 |
| 5,188,126 A | 2/1993 | Fabian et al. | ................. | 128/899 |
| 5,190,059 A | 3/1993 | Fabian et al. | ................. | 128/899 |
| 5,329,944 A | 7/1994 | Fabian et al. | ................. | 128/899 |
| 5,447,511 A * | 9/1995 | Gadd | .......................... | 606/131 |
| 5,664,582 A | 9/1997 | Symaitis | ...................... | 128/898 |
| 5,923,001 A | 7/1999 | Morris et al. | ................. | 177/245 |
| 5,931,824 A | 8/1999 | Stewart et al. | ............... | 604/358 |
| 6,026,818 A | 2/2000 | Blair et al. | ................... | 128/899 |
| 6,359,563 B1 | 3/2002 | Herzer | ...................... | 340/572.6 |
| 6,407,676 B1 | 6/2002 | Tanji et al. | ................... | 340/993 |
| 6,632,228 B2 * | 10/2003 | Fortier et al. | ................. | 606/140 |
| 6,840,943 B2 * | 1/2005 | Kennefick et al. | ........... | 606/104 |
| 2002/0005783 A1 | 1/2002 | Irizarry et al. | ........... | 340/572.1 |

* cited by examiner

*Primary Examiner*—Tatyana Zalukaeva
*Assistant Examiner*—C. Lynne Anderson
(74) *Attorney, Agent, or Firm*—Ernest D. Buff & Associates; Ernest D. Buff; Theodore J. Pierson

(57) ABSTRACT

Externally detectable electronic article surveillance markers are attached to surgical implements, such as sponges and surgical instruments, appointed for use in a surgical wound. The attachment mechanism facilitates detection by an external interrogating field before the wound has been closed and the patient has left the operating table. The markers are responsive to the imposition of an interrogating field produced by an electronic article surveillance system. Use of the attachment mechanism and markers assure that the surgical implements are reliably detected and removed before completion of the surgical procedure. This technique eliminates the not infrequent mishap in which an implement is undiscovered at the time of surgery and remains indefinitely within the surgical cavity, often entailing dire consequences to the patient.

7 Claims, 6 Drawing Sheets

ATTACHMENT OF ELECTRONIC TAGS TO SURGICAL SPONGES AND IMPLEMENTS

BACKGROUND OF THE INVENTION

1. Field of the Invention

The present invention relates to markers for electronic article surveillance systems; and more particularly, to attachment means for affixing markers to surgical sponges and other implements, thereby permitting them to be detected by the article surveillance system.

2. Description of the Prior Art

During the course of a surgical operation it is generally necessary for articles, such as surgical sponges, gauzes, instruments and the like, to be placed into a wound cavity. Despite rigorous attention given to locating these items and ensuring removal of all of them prior to completion of the surgical procedure and closure of the surgical incision, such items are sometimes overlooked and remain within the patient. When this occurs, serious consequences often ensue. The patient may suffer pain, infection, intestinal obstruction, and even death. If this mishap is discovered, an additional invasive surgical procedure is essential to remove the foreign object to prevent serious, and possibly fatal, consequences to the patient. The severity of the problem of retained surgical implements has been recognized since the earliest days of surgery. The procedures traditionally employed to prevent post-surgical implement retention include manual search of the wound by the surgeon prior to closure and a careful accounting for all materials inserted and removed from the wound. This accounting function is customarily carried out by the operating room staff, usually the circulating nurse. Notwithstanding these precautionary measures the accidental retention of surgical implements continues to occur to this day with disturbing regularity, even in highly respected institutions. Surgeons and related medical professionals regard this eventuality as a major unsolved problem.

At present, physical count combined with manual search of the wound cavity prior to wound closure remain the primary protocol used for detecting retained surgical implements. Nevertheless, the above-mentioned shortcomings of the protocol have led to other approaches, such as the use of x-ray methods. Most surgical instruments are composed of metal, and are easily visible on x-ray. Sponges are generally made to bear a radiopaque component to make them also visible on x-ray. However, intraoperative x-rays are not routinely performed before closure of the incision for several reasons: They entail the risk of extension of operative time and anesthesia, along with undesirable expense, inconvenience, and radiation exposure. Postoperative x-rays are subject to some of the same disadvantages and are not routinely done unless there is a specific question or suspicion of a retained implement in a given case. Moreover, even when postoperative x-rays are obtained, retained surgical implements are still overlooked in many cases, owing to the presence of artifacts or other competing shadows on the film or the unfavorable orientation of the object relative to the x-ray incidence direction and the position of the x-ray film. If a retained article is detected, a timely second operation is required to effect its removal, notwithstanding the further trauma to the patient. The severity of the problem clearly warrants efforts that allow the aforementioned consequences to be avoided altogether by ensuring removal of the offending articles before surgery is completed, not at a later point.

Over the years many efforts have been made to prevent the accidental retention of surgical implements. U.S. Pat. Nos. 5,057,095, 5,107,862, 5,190,059, 5,329,944, 5,105,829, and 5,188,126 to Fabian et al. disclose the use of various technologies to detect surgical implements marked with a tag and left within the surgical wound after completion of surgery and prior to closing the wound. Despite these and other disclosures, the use of externally detectable markers has not yet become a part of routine hospital practice. Among the remaining impediments is the need for reliable and convenient means of affixing such markers to surgical items. Suitable means must satisfy a number of requirements. Any item used invasively must be capable of being appropriately sanitized and sterilized prior to use. Attachment means are especially sought that do not compromise the functionality of the surgical item or unduly restrict the ability of the surgeon or other assistant to see and access the operation site and to manipulate and use the item in an optimal manner for its intended primary function. The item should not harm the patient and should be compatible with the surgical environment and not be degraded in the presence of bodily fluids and other substances encountered during surgery.

SUMMARY OF THE INVENTION

The present invention provides means for attaching an externally detectable marker to a surgical implement. Such a surgical implement, when used during a procedure carried out in an operating room is sometimes inadvertently retained within the wound. A marker, when affixed to the surgical implement, allows it to be detected while the patient is still on the operating table. The attachment means associates the marker with the surgical implement in a highly reliable manner, thereby assuring detection of surgical implements accidentally left within the wound during surgery. A wide variety of implements used in the course of surgery may be tagged in accordance with the present invention. These implements notably include surgical sponges and surgical instruments.

As used herein, the term "surgical sponge" refers to a variety of fabric-type articles used to protect body tissues and to absorb blood and other fluids and substances encountered during surgery. Surgical sponges are typically planar and square or rectangular in shape and are generally comprised of a plurality of layers of woven or non-woven fabric. The fabric may be composed of either natural fibers like cotton or synthetics including nylon, rayon, polyester, and acrylics. The sponge optionally comprises non-absorbent surface layers and absorbent interior layers. Sponges are widely used during surgical procedures to absorb blood and other bodily fluids present in the surgical field and as a protective interface between an organ (or other internal body part) and surgical instruments used to manipulate and secure the organ in a displaced position facilitating a surgeon's access to another body structure otherwise obscured. A sponge is also sometimes secured to the orifice of a suction tube to prevent injury that may occur, for example, if the tube becomes rigidly attached to an internal body structure or tissue. The term "surgical sponge" further includes any other similar absorbent device such as a wound dressing and an absorbent device attached to a holder, such as an absorbent swab.

The term "surgical instrument" is used herein to mean any rigid or semi-rigid implement inserted through a surgical incision or wound into a cavity in an area requiring surgical treatment and typically is manipulated by a surgeon in carrying out surgical treatment. A wide variety of surgical instruments are known, including, but not limited to, cutting devices such as scissors, scalpels, and drills; holding and clamping devices such as forceps, hemostats, and suture holders, and other miscellaneous implements including retractors, probes, suction tubes, and drainage tubes.

The surgical item and marker of the invention are adapted for use in conjunction with an electronic article surveillance (EAS) system. An EAS system comprises means for generating within an interrogation zone an interrogating field, a marker responsive to the presence of the interrogating field, detection means for detecting the response of the marker, and indicating means for alerting a system user to the presence of the marker. The present method and article may be employed in conjunction with any EAS system having these attributes and capable of being operated in the context of a medical facility.

It will be understood that while the present invention is described in connection with the treatment of humans, the articles and methods set forth herein may also be applied in the veterinary treatment of animals.

In an aspect of the invention there is provided a surgical sponge system comprising: (i) a surgical sponge having a pocket for receiving a remotely detectable electronic marker; (ii) a flap for closing the pocket, the flap having at least one side hingedly attached to the surgical sponge; (iii) fastening means for closing and securing the flap to the surgical sponge in the closed position; and (iv) a remotely detectable electronic marker inserted within the flap. Advantageously, the described sponge system allows detection and removal of a sponge prior to completion of a surgical procedure in which it is used.

In another aspect a surgical sponge system comprises a surgical sponge, a remotely detectable, magnetomechanically resonant electronic marker, and attachment means for attaching the marker to the surface of the sponge.

In still another aspect a surgical instrument system comprises a surgical instrument having a tag connection aperture; an electronic tag, and securing means for securing the tag to the instrument at the aperture.

BRIEF DESCRIPTION OF THE DRAWINGS

The invention will be more fully understood and further advantages will become apparent when reference is had to the following detailed description of the preferred embodiment of the invention and the accompanying drawings, in which.

DESCRIPTION OF THE PREFERRED EMBODIMENTS

The present invention provides a surgical implement having attached thereto an externally detectable marker. The surgical implement is any of a wide variety of devices appointed to be placed into a surgical wound cavity during a surgical procedure, typically including sponges, gauzes, instruments, probes, and clamping or cutting devices. The remote detectability of the marker allows detection and removal of the implement prior to completion of the surgery, thereby eliminating the severe consequences that arise from retained articles. Referring generally to FIGS. 1 to 15 of the drawings, there are shown a variety of means for affixing an externally detectable marker to a surgical implement.

The marked items of the invention may be used in conjunction with any EAS system capable of sensing and remotely detecting a marker and compatible with the requirements of safe operation in the context of a medical venue. A wide variety of such EAS systems are currently known, including microwave, RF, and magnetic systems. Some of these systems employ substantially identical markers (also known as tags). These tags generate a response to an interrogating field produced by the EAS system that unambiguously indicates the presence or absence of a marker. However, the system cannot differentiate the response of individual tags from other substantially identical tags. One such system is the magnetomechanically actuated article surveillance system disclosed by U.S. Pat. Nos. 4,510,489 and 4,510,490. Another system is the harmonic-responsive article surveillance system disclosed by U.S. Pat. RE No. 35,042. Other systems have now become available in which each marker has a unique signature that is remotely recognizable by the detection system. Such a marker, often known as a "smart" marker or transponder, frequently comprises electronic circuitry that is activated by an interrogating field and in response the marker transmits an identifying code unique to that specific marker. One type of smart marker is commercially available from Texas Instruments under the tradename "TIRIS." Most of the EAS systems employing smart markers are RF systems, i.e., they use an RF electromagnetic field as the interrogation field and the marker generates or modifies an RF field in response.

Many markers suitable for use in the practice of the present invention comprise an active element that is encased in a plastic housing comprising some means allowing the marker to be attached to another item. The term "marker" is used herein to refer generically to the combination of the active element and any housing or related mounting means. In addition, it will be understood that a marker may include more than one active element, which elements may be responsive to EAS systems of different types. It will also be appreciated that more than one marker may be attached to a given surgical item to further improve its detectability or to allow detection by EAS systems of different types.

Figure 1:
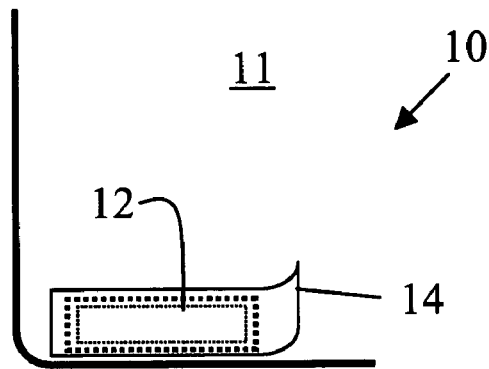
FIG. 1 is a partial plan view depicting a corner of a surgical sponge and a marker affixed thereto by a pressure-sensitive tape.
Figure 2:
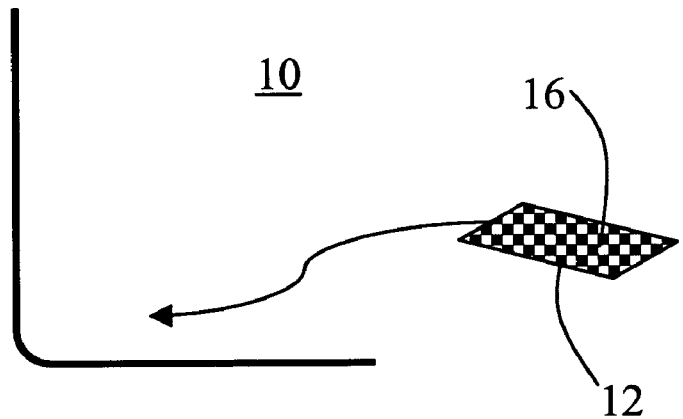
FIG. 2 is a partial plan view depicting a corner of a surgical sponge and a marker adapted to be affixed to the sponge using an adhesive present on the marker.
Figure 3:
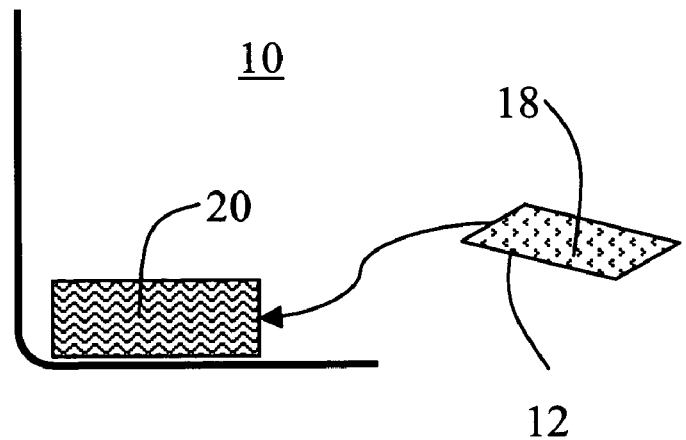
FIG. 3 is a partial plan view depicting a corner of a surgical sponge and a marker adapted to be affixed to the sponge using a hook and loop fastening system.

In some aspects of the invention the surgical implement is a sponge, at least a portion of which is generally composed of absorbent material. Referring now generally to FIGS. 1-3, there is depicted a surgical sponge system including a surgical sponge 10 having a surface and a marker 12 which is affixed to the surface by attachment means. At least a part of sponge 10 is an absorbent portion 11. It will be understood by one skilled in the art that marker 12 may be located at any place on the surface of sponge 10, but that marker 12 is preferably disposed proximate an edge of sponge 10. More preferably, as shown in FIGS. 1-3, marker 12 is positioned proximate a corner of sponge 10 to minimize the marker's effect on the conventional use of sponges in surgery. In the aspect depicted by FIG. 1 the attachment means comprises a pressure sensitive tape 14 applied over marker 12 to secure it to the surface of sponge 10. In another aspect, marker 12 is attached to sponge 10 by an adhesive 16 as shown in FIG. 2. The adhesive 16 is shown in FIG. 2 as being applied to marker 12 prior to its placement on sponge 10, but it may also be applied at a suitable place to the sponge or to both sponge and marker to assure adequate adherence. In another aspect, depicted by FIG. 3, attachment means comprises a hook and loop attachment system of the type commonly known by the tradename VELCRO. The VELCRO system comprises a hook portion 18 and a loop portion 20, one of which is affixed to marker 12 and the other to sponge 10. Engagement of the hook and loop portions attaches marker 12 to sponge 10.

Figure 4:
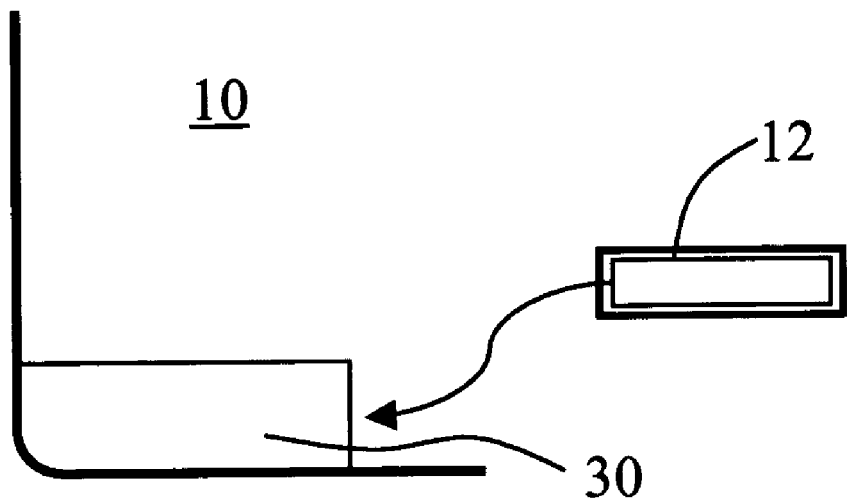
FIG. 4 is a partial plan view depicting a corner of a surgical sponge having a pocket adapted to receive and house a marker.
Figure 5:
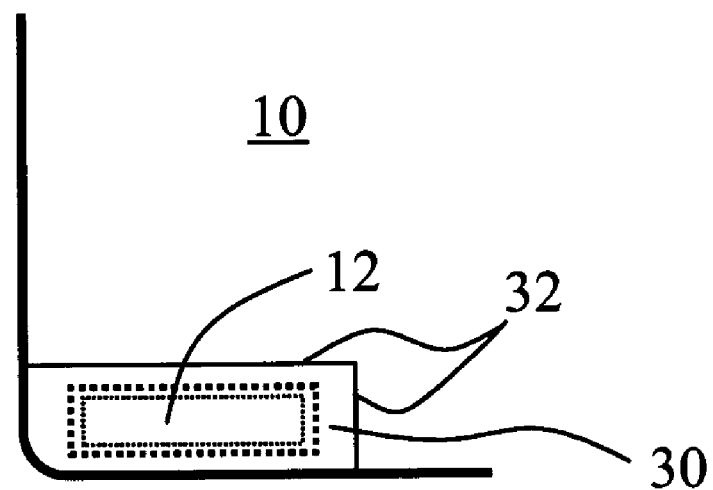
FIG. 5 is a partial plan view depicting a corner of a surgical sponge having a pocket that has been sewn closed after insertion of a marker.

In other aspects of the invention, depicted by FIGS. 4-5, sponge 10 is provided with a pocket 30 having a size sufficient to receive and house a marker. Pocket 30 may be positioned at any locations on the surface of sponge 10, but preferably is proximate an edge or corner thereof, as shown in FIGS. 4-5. Pocket 30 preferably is sized to hold marker 12 in a substantially fixed position within sponge 10. A number of methods may be used to form pocket 30, including, but not limited to, sewing. In aspects in which sponge 10 comprises fusible materials, heat fusion or sealing may be used to prepare pocket 30 and to secure marker 12 within boundaries 32 of pocket 30, as depicted by FIG. 5.

Figure 6:
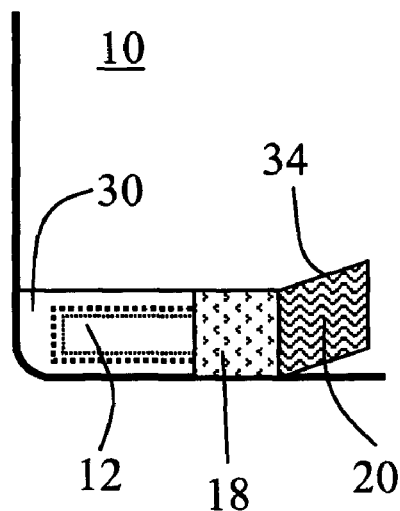
FIG. 6 is a partial plan view depicting a corner of a surgical sponge having a pocket adapted to receive and house a marker and a hinged flap adapted to close the pocket, the flap being secured closed by a hook and loop fastening system.
Figure 7:
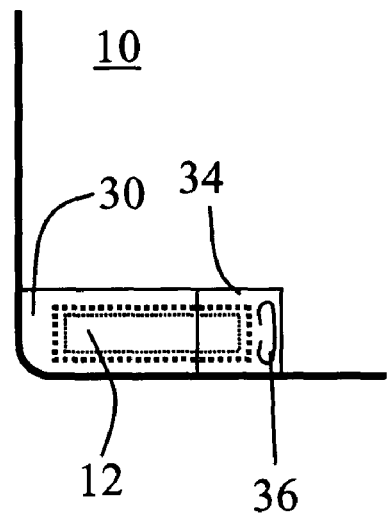
FIG. 7 is a partial plan view depicting a corner of a surgical sponge having a pocket adapted to receive and house a marker and a hinged flap adapted to close the pocket, the flap being secured closed by a staple.
Figure 8:
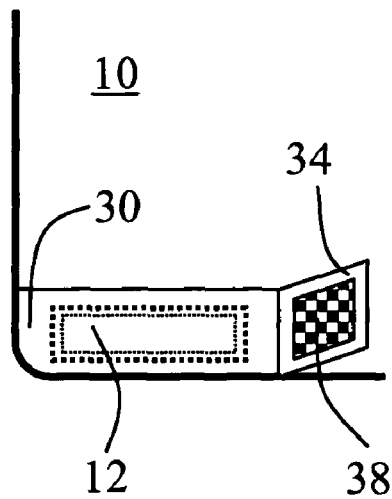
FIG. 8 is a partial plan view depicting a corner of a surgical sponge having a pocket adapted to receive and house a marker and a hinged flap adapted to close the pocket, the flap being secured closed by an adhesive.
Figure 9:
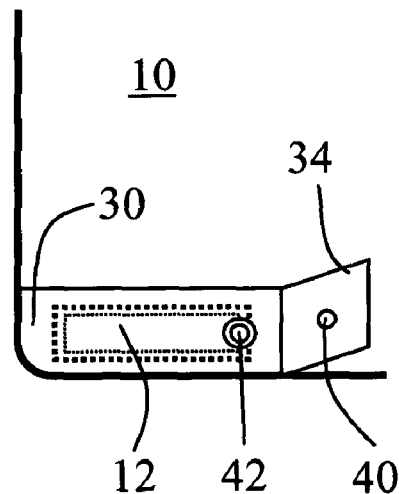
FIG. 9 is a partial plan view depicting a corner of a surgical sponge having a pocket adapted to receive and house a marker and a hinged flap adapted to close the pocket, the flap being secured closed by a snap system.

In still other aspects of the invention depicted by FIGS. 6-9, sponge 10 is provided with a pocket 30 for receiving and housing a marker 12. Flap 34 is hingedly attached on one of its sides to sponge 10. Marker 12 is disposed in pocket 30 and secured therewithin by closure of flap 34. A fastening means is used to maintain flap 34 in the closed position, thereby securing marker 12. FIG. 6 depicts an aspect in which the fastening means comprises a hook and loop closure system of the type commonly known by the tradename VELCRO. The VELCRO system comprises a hook portion 18 and a loop portion 20, one of which is affixed to flap 34 and the other to sponge 10. The hook and loop portions 18, 20 are positioned for mutual engagement when flap 34 is in the closed position. In the aspect depicted by FIG. 7 the fastening means comprises a staple 36 closing flap 34. FIG. 8 depicts another alternative, the use of an adhesive 38. The adhesive 38 is shown as being placed on flap 34, but may optionally be applied at a suitable place to sponge 10 or to both areas. A snap system comprising a first snap 40 in flap 34 and a second snap 42 in sponge 10 comprises the fastening means of the aspect shown in FIG. 9. Snaps 40 and 42 are mutually engageable upon closure of flap 34. In still other aspects (not shown), flap 34 may be sewn closed, closed by heat sealing, or closed by application of a pressure sensitive tape such as adhesive tape. Other suitable fastening means will be apparent to one skilled in the art.

Figure 10:
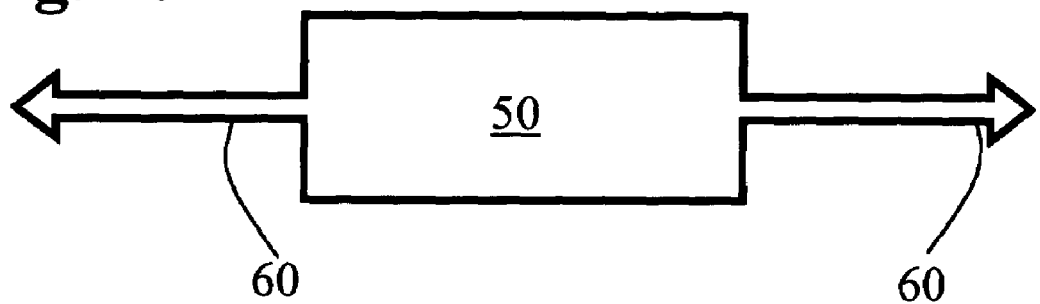
FIG. 10 is a plan view of a marker having two anchors for attachment of the marker to a surgical sponge or implement, the anchors being integral with the marker.
Figure 11:
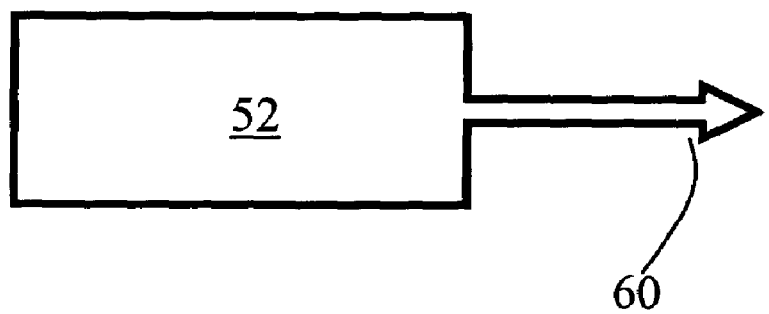
FIG. 11 is a plan view of a marker having an anchor for attachment of the marker to a surgical sponge or implement, the anchor being integral with the marker.
Figure 12:
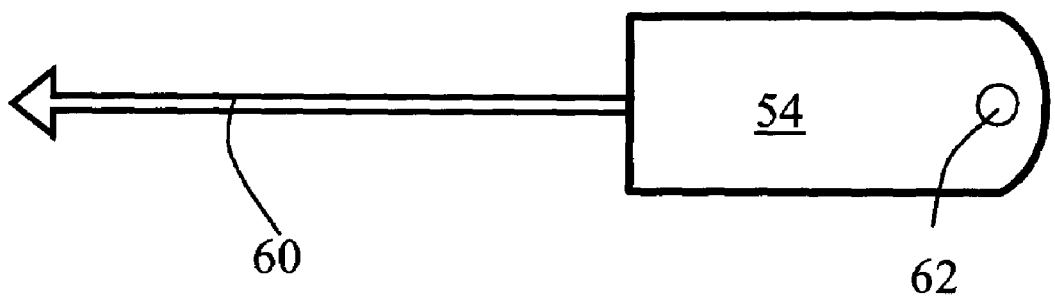
FIG. 12 is a plan view of a marker having an anchor at one end and an eyelet at the opposite end, the eyelet being appointed to receive the anchor to form a loop for attaching the marker to a surgical sponge or implement.
Figure 13:
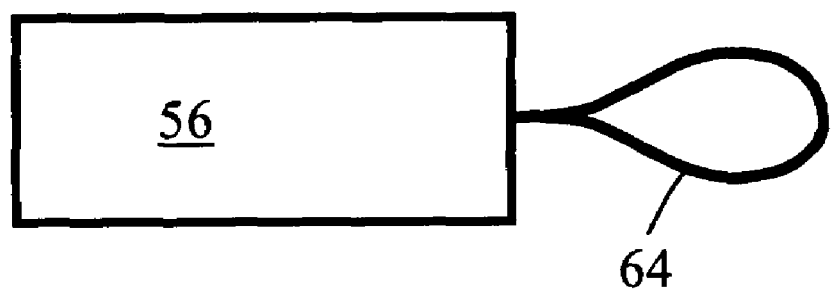
FIG. 13 is a plan view of a marker having a loop for attachment of the marker to a surgical sponge or implement, the loop being integral with the marker.
Figure 14:
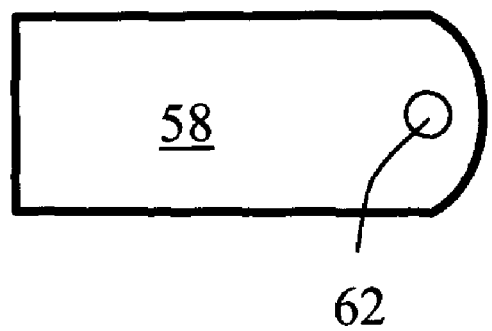
FIG. 14 is a plan view of a marker having an eyelet therein for attachment of the marker to a surgical sponge or implement.

FIGS. 10 to 14 depict forms of markers useful in the practice of the present invention and having structures that may be used to attach the marker to a surgical sponge or surgical implement. The markers depicted by FIGS. 10 and 11 incorporate one or more elongated anchors that depend from the body of the marker and have a barb at the free end. The free, barbed end is resiliently deformable, allowing it to be inserted into an aperture and secured thereto. Preferably the marker is difficult or impossible to remove after being thus secured. In an aspect of the invention the barbed end is split axially to allow it to be compressed for insertion in an undersized aperture. After insertion, the barbed end returns to its normal size, which prevents it from being withdrawn from the aperture. FIG. 10 depicts a marker 50 having two oppositely disposed, elongated anchors 60 integral with the marker and usable for anchoring the marker. FIG. 11 depicts a similar marker 52 having one elongated, integral anchor 60. FIG. 12 depicts a marker 54 having an eyelet 62 at one end and an elongated anchor 60 depending from the other end. The anchor 60 is adapted to be inserted irreversibly through eyelet 62 to form a loop by which the marker may be secured to an object by passage through an aperture. A loop 64 having two ends attached to a marker 56 is seen in FIG. 13. The loop 64 is constructed of a polymer, a textile thread, cord, or the like for attachment to a surgical article. The marker 58 of FIG. 14 has an eyelet 62 through which a lanyard, composed of polymer, textile fiber, or the like, may be passed for attachment to a surgical item.

Figure 15:
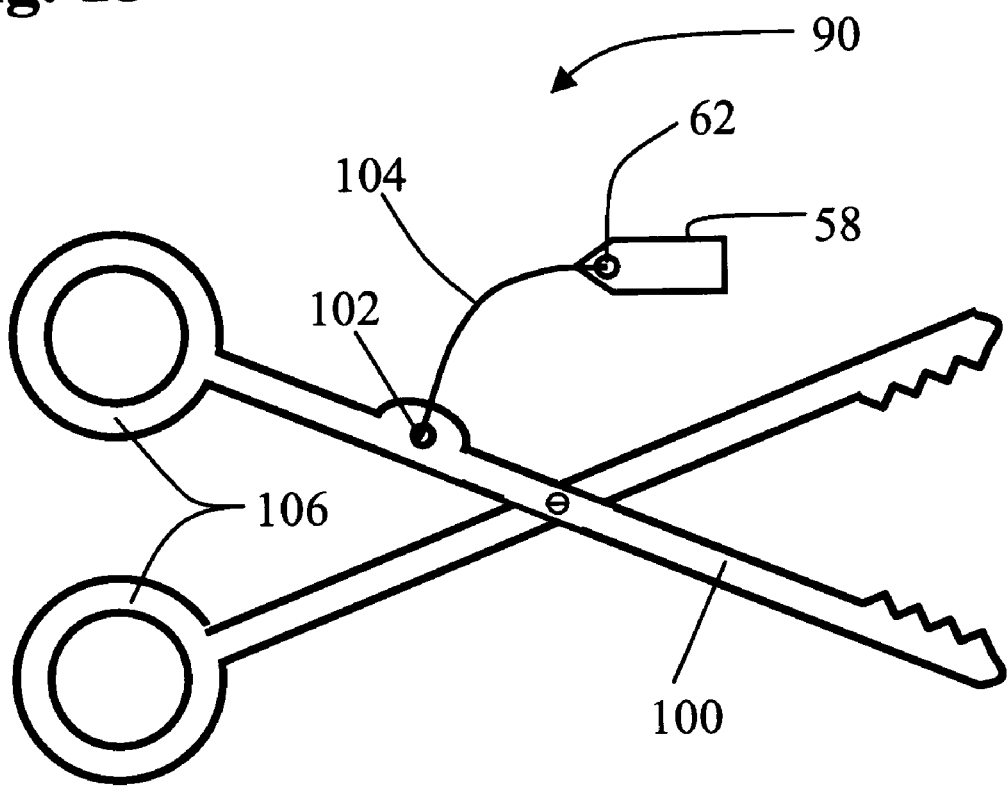
FIG. 15 is a perspective view of a surgical implement system having an aperture, a marker, and a lanyard attaching the marker to the aperture.

The present invention further provides a surgical instrument system having an attached marker. In some aspects the surgical instrument system comprises a surgical instrument having a tag connection aperture and an electronic tag secured to the instrument by a securing means. FIG. 15 depicts a surgical instrument system 90 comprising a surgical instrument 100 and a marker 58 of the type depicted by FIG. 14 and the securing means comprises a lanyard 104 linking eyelet 62 of marker 58 to tag connection aperture 102 present in surgical instrument 100. It will be appreciated that other markers, especially including those depicted by FIGS. 11-13, may also be used in constructing system 90. Other securing means recognizable to those skilled in the art are also useful in constructing the surgical instrument system of the invention, including use of rivets or screws to attach the marker.

The selection of a suitable securing means and proper location of aperture 102 beneficially enhance the functionality of system 90. It is preferred that the marker of system 90 be sufficiently removed from the handle of system 90 so that it does not inconvenience the surgeon in comfortably grasping the instrument at its handle. At the same time, it is also preferred that the marker not intrude into the region wherein the instrument is performing its intended function. However in some aspects the detectability of the marker is beneficially enhanced by use of a lanyard or anchor that places it 1-3 cm away from a metal instrument which might partially shield the marker from an interrogating field.

Figure 16:
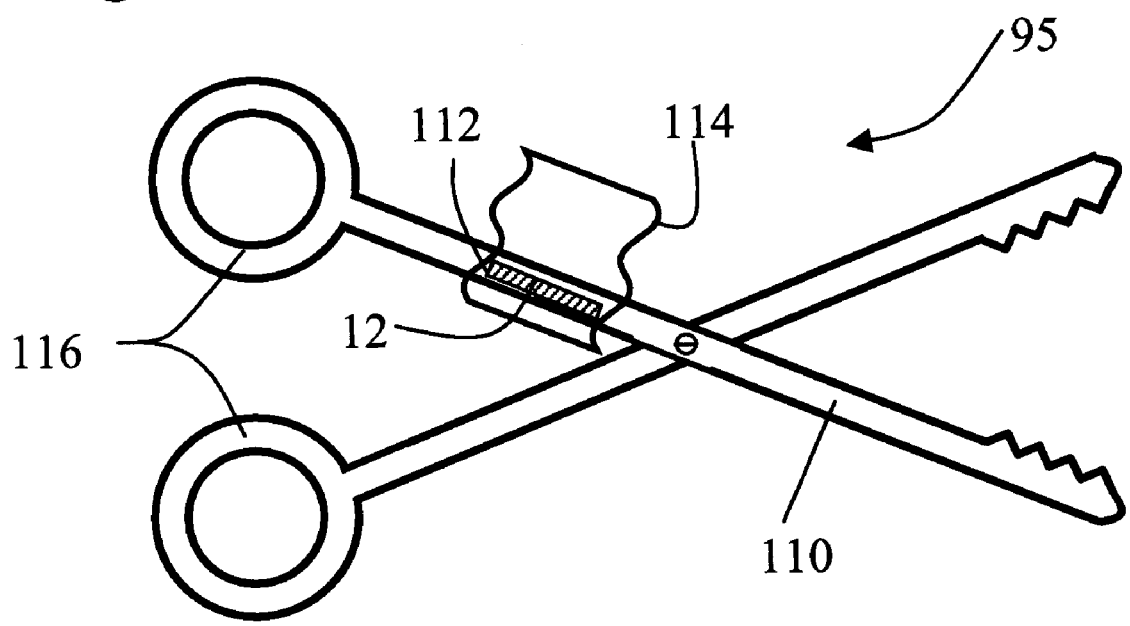
FIG. 16 is a perspective view of a surgical implement system comprising a surgical implement having an indentation adapted to receive and house a marker, the marker being secured in the indentation by a pressure-sensitive tape.

Still another aspect of a surgical instrument system 95 of the invention is depicted by FIG. 16. Surgical instrument 110 has an indented well 112 sufficient in size to accommodate an electronic tag 12. Well 112 is depicted by FIG. 16 as having the shape of a generally rectangular prism open on one of its faces. Other shapes of well are also advantageous in the practice of the invention, including shapes in which at least one other wall is also open, instead of being closed as depicted by FIG. 16. A tag 12 is disposed in well 112 and secured therewithin by any suitable means. In the aspect seen in FIG. 16, well 112 is covered by a pressure sensitive tape 114 to close the well and secure tag 12. In other aspects tag 12 is secured using an adhesive or by a cover plate covering well 112 and attached to instrument 110 by at least one screw, rivet, or the like.

The surgical sponge system and surgical instrument system of the present invention are advantageously used in carrying out a wide variety of medical and surgical procedures on a patient. At any time during or after such a procedure, the patient is exposed to the interrogating field of an EAS system that activates any marker present either within the patient or in close proximity. The EAS detector responds to the presence of an activated marker by causing an indication, preferably audible and/or visual, to alert the relevant personnel to the presence of a tagged item in the interrogation zone, which preferably encompasses at least the surgical site. Suitable measures can thus be undertaken. Preferably, a scan is carried out immediately before a surgical procedure is completed to ensure that all implements have been removed from the patient and properly accounted for. Moreover, a scan can be repeated even after completion of a procedure, since a tagged article can be detected within a patient even after the wound has been closed, and the article is surrounded by normal body tissue and the fluids and other substances found within a patient. Unlike previous methods for ensuring removal of surgical items, such as x-rays, the present method can be carried out quickly and conveniently, even in the rigorous working environment of an operating room. The surgical items and the ancillary equipment, such as the EAS electronics, are compatible with such requirements as proper sterilization and safety.

Having thus described the invention in rather full detail, it will be understood that such detail need not be strictly adhered to but that various changes and modifications may suggest themselves to one skilled in the art, all falling within the scope of the invention as defined by the subjoined claims.

What is claimed is:

1. A surgical sponge system, comprising:
   a) a surgical sponge having a pocket for receiving a remotely detectable electronic marker;
   b) a flap for closing said pocket, said flap having at least one side hingedly attached to said surgical sponge;
   c) fastening means for closing and securing said flap to said surgical sponge in the closed position, wherein said fastening means comprises a first snap in said flap and a second snap in said sponge, said first and second snaps being mutually engageable; and
   d) a remotely detectable electronic marker inserted within said flap.

2. A surgical sponge system as recited by claim 1, wherein said sponge has at least one corner and said pocket is positioned proximate said corner of said sponge.

3. A surgical sponge system as recited by claim 1, wherein said sponge has at least one edge and said pocket is positioned proximate said edge of said sponge.

4. A surgical sponge system, comprising:
   a) a surgical sponge having a pocket for receiving a remotely detectable electronic marker;
   b) a flap for closing said pocket, said flap having at least one side hingedly attached to said surgical sponge;
   c) fastening means for closing and securing said flap to said surgical sponge in the closed position, wherein said fastening means comprises a hook and loop fastening system having a hook portion and a loop portion, one of said hook portion and said loop portion being affixed to said flap and the other of said hook portion and said loop portion being affixed to said sponge, said hook portion and said loop portion being positioned for mutual engagement; and
   d) a remotely detectable electronic marker inserted within said flap.

5. A surgical sponge system, comprising:
   a) a surgical sponge;
   b) a remotely detectable, magnetomechanically resonant electronic marker; and
   c) attachment means for attaching said marker to a surface of said surgical sponge, wherein said fastening means comprises a hook and loop fastening system comprising a hook portion and a loop portion, one of said hook portion and said loop portion being affixed to said marker and the and the other of said hook portion and said loop portion being affixed to said surgical sponge.

6. A surgical sponge system as recited by claim 5, wherein said sponge has at least one corner and said marker is attached proximate said corner.

7. A surgical sponge system as recited by claim 5, wherein said sponge has at least one edge and said marker is attached proximate said edge.

* * * * *